United States Patent [19]

Imrie et al.

[11] Patent Number: 4,990,501

[45] Date of Patent: Feb. 5, 1991

[54] FILM FORMING COMPOSITION FOR TOPICAL USE

[75] Inventors: Frazer K. E. Imrie, Reading, United Kingdom; Ken James, Grove, England

[73] Assignee: Sempernova PLC, Reading, England

[21] Appl. No.: 23,859

[22] PCT Filed: Jun. 11, 1986

[86] PCT No.: PCT/GB86/00333

§ 371 Date: Mar. 26, 1987

§ 102(e) Date: Mar. 26, 1987

[87] PCT Pub. No.: WO86/07255

PCT Pub. Date: Dec. 18, 1986

[30] Foreign Application Priority Data

Jun. 13, 1985 [GB] United Kingdom ............... 8514975

[51] Int. Cl.$^5$ .................. A61K 7/48; A61K 47/00; A61K 31/70

[52] U.S. Cl. ................................ 514/54; 424/401; 514/57; 514/777; 514/781; 514/859; 514/871; 514/943; 514/844

[58] Field of Search ............... 514/54, 57, 777, 781, 514/859, 871, 943, 844; 424/401; 536/119

[56] References Cited

U.S. PATENT DOCUMENTS

| 4,151,304 | 4/1979 | Evans | 536/119 |
|---|---|---|---|
| 4,298,730 | 11/1981 | Galleymore et al. | 536/119 |
| 4,334,061 | 6/1982 | Bossier | 536/119 |
| 4,379,755 | 4/1983 | Yamada et al. | 514/943 |
| 4,611,055 | 9/1986 | Yamamoto et al. | 536/119 |
| 4,797,300 | 1/1989 | Jandacek et al. | 536/119 |
| 4,822,601 | 4/1989 | Goode et al. | 514/54 |

FOREIGN PATENT DOCUMENTS 1317548 1/1963 France.
2182935 4/1973 France.

OTHER PUBLICATIONS

The Merck Index, 10th edition, published by Merck & Co., Inc., Rahway, N.J., U.S.A., 1983, p. 771, item 5191.

*Primary Examiner*—Ronald W. Griffin
*Attorney, Agent, or Firm*—Bachman & LaPointe

[57] ABSTRACT

A composition for application to human and animal tissue surfaces, said composition comprising an aqueous medium and a film-forming component at least partially soluble or dispersible in said aqueous medium, said film-forming component comprising an ester or mixture of esters, at least one being an ester of a polyol.

15 Claims, No Drawings

FILM FORMING COMPOSITION FOR TOPICAL USE

This invention relates to compositions and more particularly concerns compositions which have medical application.

More specifically, the invention relates to compositions which are useful for the treatment of human and animal tissue surfaces, for example skin. Compositions have been found particularly useful for the treatment of skin ailments such as acne and also for injuries where the skin has been damaged, such as burns.

According to one aspect of the present invention we provide a composition for application to human and animal tissue surfaces, said composition comprising an aqueous medium and a film-forming component at least partially soluble or dispersible in said aqueous medium, said film-forming component comprising an ester or mixture of esters, at least one being an ester of a polyol.

In a preferred embodiment, the aqueous medium comprises water and the film forming component comprises a sucrose ester or mixture of sucrose esters, wherein the quantity or sucrose ester of mixture of sucrose esters is 40% to 80% (w/w) of the composition excluding the water.

The film-forming component is preferably soluble in water to an extent of at least 5% by weight at 25° C., more preferably at least 10% by weight.

In preferred compositions according to the invention mixtures of esters are employed, mixtures containing saturated and unsaturated fatty acid esters being particularly preferred. Ratios in the range 20 to 100% by weight saturated to 0-80% unsaturated can be employed. Generally however it is advantageous to include at least 10% by weight unsaturated fatty acid ester in the ester mixture comprising the film-forming component.

It is believed that the presence of unsaturated fatty acid ester helps to solubilise saturated fatty acid esters which if used above would be insoluble. The at least partial solubility or dispersibility of the ester mixture is believed to be necessary in order to achieve a coherent film on a tissue surface being treated with the composition.

The choice of fatty acid esters depends to some extent on the solubility or dispersibility. Thus saturated fatty acid esters which are insoluble in water are suitable only if used in mixtures with esters which have a solubilising effect.

Saturated fatty acid esters in the range $C_8$ to $C_{22}$ can be employed but esters in which the fatty acid is in the range $C_{12}$ to $C_{22}$ are generally insoluble and thus require to be used in mixtures with solubilising esters. In such mixtures saturated fatty acids in the range $C_{12}$ to $C_{20}$ are preferred, especially $C_{16}$ to $C_{18}$.

The esters of unsaturated fatty acids are preferably derived from fatty acids in the range $C_{16}$ to $C_{22}$, preferably $C_{16}$ to $C_{18}$.

The polyol may be a sugar, especially sucrose, but other polyols may be used, including lactitol, sorbitol, sorbitan and polyglycerol.

Mixtures of sucrose esters have been found to be advantageous, especially mixtures of sucrose stearates, palmitates and/or oleates.

The composition may include further ingredients to improve its properties or ease of application. The addition of a thickening agent has been found to give desirable properties, suitable thickening agents being cellulose and cellulose derivatives, such as carboxymethyl celluloses.

An additive which improves the "feel" of the composition when applied to the tissue surface may also be included. One such additive is a mixture of mono and diglycerides although other materials could be employed for this purpose, such as lanolin, jojoba oil, coconut oil and similar materials.

The composition may be in the form of a solution, suspension or emulsion. Where the composition is to be used as a treatment for skin ailments or as an application to tissue it is often preferable for the composition to be in the form of an emulsion and to this end it is desirable to add one or more emulsifying agents.

The choice of sucrose ester or esters will to some extent depend upon the end use of the compound. The amount of saturated fatty acid ester may be from 20% to 100% and the amount of unsaturated fatty acid in admixture with the saturated ester may be 0 to 80%.

The total quantity of sucrose esters may comprise 20% to 100% of the composition (excluding the solvent or carrier medium) preferably 40% to 80% and more preferably 50% to 75%. The thickening agent may comprise 0 to 60% of the composition preferably 10% to 50% and more preferably 15% to 40%.

The viscosity of the composition in the temperature range of 20° C. to 35° C. may be 2000 to 10000 poise, preferably 3000 to 6000 poise, more preferably 3500 to 4500 poise. At 20° C. the viscosity is most preferably substantially 4500 poise, and at 35 ° C. the viscosity is most preferably substantially 3500 poise.

The above viscosities were determined using a machine called "Brookfield Model LV" with spindle number 4 and a speed setting of 0.3.

In the following Examples the basic formulation comprises 64% sucrose ester mixture, 26% sodium carboxymethyl cellulose and 10% food emulsifier, all percentages being on a dry weight basis. The sucrose ester mixture is 70% sucrose mono/di stearate and 30% sucrose mono/di oleate.

EXAMPLE 1

The product was applied as a 20% w/v paste. Product was smeared on to the facial skin rubbing it in well as when using a lotion. This was done immediately before retiring for the night. The product dried to produce a flexible film rather than a cosmetic face pack.

In the morning the film was removed by washing with cold water.

The subject's face was extremely spotty before treatment began. Within 7 days the spots had begun to clear and within 14 days had disappeared completely.

EXAMPLE 2

In this instance a second subject was treated using the same technique as in Example 1. The test area was the chin of the subject immediately below the lower lip. Only half of the area was treated and care was taken to see that the untreated half did not come into contact with the product during the morning wash. In this case the spots cleared up on the treated portion of the skin but not on the untreated area.

EXAMPLE 3

The same subject as in Example 1. All details as in Example 1 but the area of skin treated was the front and back of the torso. Again, complete clearance of spots within 14 days.

EXAMPLE 4

A third subject was treated by washing twice daily (morning and night) with a 2% w/v solution of the formulation (same composition as in Example 1 on a dry-basis) in place of soap and water. Spots began to disappear and within 7 days had almost gone. The subject then discontinued the treatment. Within 4 days the spots had returned. When treatment was recommenced the spots again started to disappear.

EXAMPLE 5

The following composition was used in clinical trials for the treatment of acne, the proportions being expressed as percentages by weight.

| | |
|---|---|
| sucrose oleate[1] | 3.5 |
| sucrose stearate[2] | 4.6 |
| mono/diglyceride | 1.3 |
| sodium carboxymethyl cellulose | 3.6 |
| preservative | 0.7 |
| water | to 100.0 |

[1] mono/diester ratio 70/30; fatty acid profile 70% oleic acid.
[2] mono/diester ratio 75/25; fatty acid profile 70% stearic acid.

The amount of sodium carboxymethyl cellulose is sufficient to produce a cream suitable for application to the skin. The trials showed a definite improvement in a significant proportion of acne sufferers treated with the cream.

EXAMPLE 6

A further composition comprises the following ingredients, the proportions being expressed as percentages by weight:

| | |
|---|---|
| S 1670[3] | 4.6 |
| OWA 1570[4] | 3.4 |
| sodium carboxymethyl cellulose | 3.0 |
| mono/diglyceride | 1.9 |
| p-hydroxybenzoic acid esters (preservative) | 0.7 |
| water | to 100.0 |

[3] S1670 is a mono/diester mixture (ratio 75/25) prepared from hydrogenated tallow (fatty acid profile 70 stearate/30 palmitate).
[4] OWA 1570 is a sucrose mono/diester (ratio 70/30) based on oleic acid.

This composition was used in clinical trials for the treatment of skin disorders including acne and improvements were demonstrated in a significant proportion of cases.

The above Examples illustrate the beneficial effects of compositions according to the invention in the treatment of skin ailments.

Whilst the invention is not intended to be limited by any theoretical explanation, it is believed that the effectiveness of the compositions may be due to physical properties of the film formed on the tissue, bacteriostatic or fungistatic properties of the esters, or a combination thereof.

The above Examples demonstrate that the compositions have beneficial effects in the treatment of skin ailments but it has also been shown that the compositions will also find use in other medical applications. One such application is the treatment of injuries where the skin has been removed or destroyed such as burns. Application of a composition according to the invention to a burned area of tissue not only serves to improve the rate of healing but also reduces pain and scarring.

We claim:

1. A composition for application to human or animal tissue surfaces, said composition comprising water and a film forming component at least partially soluble or dispersible in said water, and said film forming component comprising a sucrose ester or mixture of sucrose esters, wherein the quantity of sucrose ester or mixture of sucrose esters is 40% to 80% (w/w) of the composition excluding the water.

2. A composition according to claim 1 in which the film-forming component is soluble or dispersible in water to an extent of at least 1% by weight at 25° C.

3. A composition according to claim 2 in which the film-forming component is soluble or dispersible in water to an extent of at least 5% by weight at 25° C.

4. A composition according to claim 3 in which the film-forming component is soluble or dispersible in water to an extent of at least 10% by weight at 25° C.

5. A composition according to claim 1 in which the film-forming component comprises a mixture of saturated and unsaturated fatty acid esters.

6. A composition according to claim 5 in which the film-forming component comprises a mixture of saturated and unsaturated fatty acid esters in the ratio of 20%–100% by weight saturated to 0–80% unsaturated.

7. A composition according to claim 6 which includes at least 10% by weight unsaturated fatty acid ester in the film-forming component and in which the unsaturated fatty acid contains 16–22 carbon atoms.

8. A composition according to claim 7 in which the unsaturated fatty acid contains 16–18 carbon atoms.

9. A composition according to claim 5 in which the saturated fatty acid contains 12–20 carbon atoms.

10. A composition according to claim 9 in which the saturated fatty acid contains 16–18 carbon atoms.

11. A composition according to claim 1 in which the film-forming component comprises an ester of palmitic, stearic and/or oleic acids.

12. A composition according to claim 1 including a viscosity modifier.

13. A composition according to claim 12 in which the viscosity modifier is cellulose or a derivative of cellulose.

14. A composition according to claim 13 in which said derivative of cellulose is carboxymethyl cellulose.

15. A composition for use in the treatment of dermatological conditions and injuries where the skin has been removed, said composition comprising water and, as an active agent, a film-forming component comprising a sucrose ester or mixture of sucrose esters wherein the quantity of sucrose ester or mixture of sucrose esters is 40% to 80% w/w of the composition excluding the water, the film-forming component being at least partially soluble or dispersible in said water, and the composition having a viscosity of 2,000 to 10,000 poise in the temperature range of 20° C. to 35° C.

* * * * *